United States Patent [19]

Ohmi

[11] Patent Number: 5,291,142
[45] Date of Patent: Mar. 1, 1994

[54] METHOD AND APPARATUS FOR MEASURING THE RESISTANCE OF CONDUCTIVE MATERIALS DUE TO ELECTROMIGRATION

[76] Inventor: Tadahiro Ohmi, 1-17-301, Komegabukuro 2-chome, Aoba-ku, Sendai-shi, Miyagi-ken 980, Japan

[21] Appl. No.: 880,219

[22] Filed: May 8, 1992

[51] Int. Cl.⁵ .............................................. G01R 27/14
[52] U.S. Cl. ................................ 324/719; 324/158 R; 324/538; 324/703; 324/713
[58] Field of Search ............... 324/703, 713, 715, 718, 324/719, 501, 537, 538, 158 R, 158 P; 165/80.2; 361/385

[56] References Cited

U.S. PATENT DOCUMENTS

| | | | |
|---|---|---|---|
| 3,710,251 | 1/1973 | Hagge et al. | 324/158 F |
| 4,483,629 | 11/1984 | Schwarz et al. | 324/703 X |
| 4,567,432 | 1/1986 | Buol et al. | 324/158 F |
| 4,739,258 | 4/1988 | Schwarz | 324/703 X |

OTHER PUBLICATIONS

"Wafer-Level J-Ramp and J-Constant Electromigration Testing . . . ", by Katto, et al., International Reliability Physics Symposium, pp. 298-305, 1991 (no month).

Primary Examiner—Kenneth A. Wieder
Assistant Examiner—Christopher Tobin
Attorney, Agent, or Firm—Baker & Daniels

[57] ABSTRACT

A testing method and apparatus for conductive materials using electric current which makes it possible to rapidly evaluate the electromigration resistance of conductive materials. The apparatus includes a substrate support for supporting a substrate on which an interconnector pattern is formed, a cooling vessel for cooling the substrate, a first current supply for applying a first current to the interconnector, a resistance measurer for measuring the resistance of the interconnector pattern while the first electric current is being applied to the interconnector pattern, a second current supply for applying a second electric current larger than the first electric current to the interconnector pattern, and a controller which controls the repetition of the measurement of resistance of the interconnector pattern and the application of the second current to the interconnector pattern.

13 Claims, 3 Drawing Sheets

METHOD AND APPARATUS FOR MEASURING THE RESISTANCE OF CONDUCTIVE MATERIALS DUE TO ELECTROMIGRATION

This invention relates to a testing method and apparatus for conductive materials using electric current, more particularly a testing method and apparatus to measure the resistance to electromigration of various conductive materials used for LSI.

BACKGROUND OF INVENTION

The prior art relating to this invention is described by using an example of interconnector materials of LSI.

At present, interconnector materials such as Al, Al-Si alloys containing several percent of Si, and Al-Si-Cu alloys containing a slight amount of Cu are used for LSI. As the integration density of LSI becomes higher, interconnectors are getting thinner and longer and the number of interconnectors is increasing. Furthermore, higher speed operation is also required for LSI as well as higher integration density. As a result, the density of the electric current flowing through interconnectors increases as LSI has higher integration density and higher quality.

However, high electric current causes atoms in metal to move in the opposite direction of the electric current and finally results in the disconnection of interconnectors. This phenomenon is known as electromigration, which is one of the most important factors in designing the reliability of metal interconnectors.

Therefore, a lot of efforts are put into the development of materials having higher resistance to electromigration to manufacture higher quality LSI. In order to shorten development period, testing methods which can evaluate the electromigration resistance of conductive materials in short time are required.

A prior art testing method of the electromigration resistance is explained below.

An amount of electric current used in LSI performance is usually less than $10^5$ A/cm$^2$. In the test, a current of about $10^6$ A/cm$^2$ is applied to interconnectors to accelerate electromigration. The test is also carried out at an ambient temperature of about 250° C. to increase the deterioration rate of interconnectors.

However, it takes a long time even in such acceleration tests until the breakdown of the interconnectors takes place: for example, it takes at least one month in the case of Al-Si alloy. Therefore, the life of interconnector is estimated from the elapsed time by which the resistance of the interconnector increases 5 or 10 percent. Nevertheless, most cases still required a few weeks to one month until the resistance increase even 5%. It will take a longer time for the materials to be developed because of higher resistance to electromigration, suggesting that these conventional methods are not a practical testing method employed during the development of new interconnector materials.

It is also found from the tests using higher current density that higher current density causes the overheating of the interconnector, resulting in the rise of the resistance of interconnector which causes the interconnect to be further heated. Namely, it is impossible to maintain the temperature of the interconnector at a prescribed value. When high current density is applied, the temperature can not be controlled and the interconnector melts to disconnection, showing that the test of electromigration can not be attained.

As mentioned above, it is actually impossible to evaluate the electromigration resistance in short period. In order to overcome above-mentioned problems, this invention is to provide a testing method and apparatus for conductive materials using electric current which makes it possible to evaluate the electromigration resistance of conductive materials in short time.

SUMMARY OF THE INVENTION

The first aim of this invention is to provide a testing method for conductive materials using electric current characterized in that the operation is repeatedly carried out wherein the resistance of an interconnector pattern made of conductive material is measured by applying a first electric current to said interconnector pattern, said interconnector pattern is heated by applying a second electric current larger than said first electric current and is simultaneously cooled from outside to control the temperature of said interconnector pattern, and then the resistance of said interconnector pattern is measured again by applying said first electric current to said interconnector pattern.

The second aim of this invention is to provide a testing apparatus for conductive materials using electric current comprising a substrate supporting means for supporting a substrate on which an interconnector pattern is formed, a cooling means for cooling said substrate, a first current supply means for applying a first current to said interconnector pattern, a means for measuring the resistance of said interconnector pattern while said first electric current is being applied to said interconnector pattern, a second current supply means for applying a second electric current larger than said first electric current to said interconnector pattern, and a controller which controls the repetitions of the measurement of the resistance of said interconnector pattern and the application of said second current to said interconnector pattern.

DETAILED DESCRIPTION OF THE PREFERRED EMBODIMENT

Figure 1:
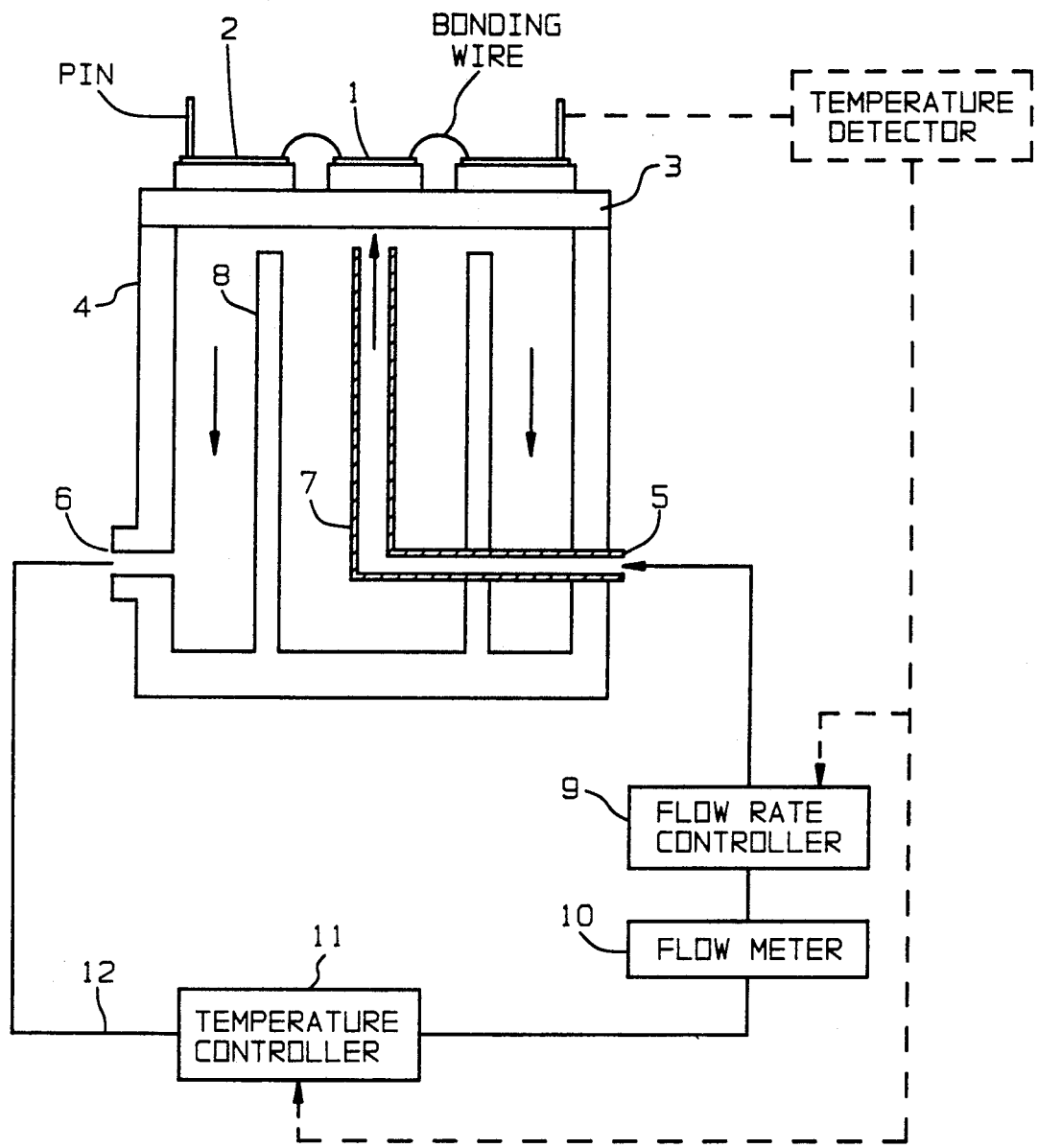
FIG. 1 is a schematic illustration of a testing apparatus for conductive materials using current.

A list of parts and numerals shown in the drawings is as follows: 1 . . . a substrate, 2 . . . a print board, 3 . . . a substrate support means, 4 . . . a vessel, 5 . . . a coolant inlet, 6 . . . a coolant outlet, 7 . . . a coolant pipe, 8 . . . a partition plate, 9 . . . a flow rate controller, 10 . . . a flow meter, 11 . . . a temperature controller, 12 . . . a pipe.

The structure of this invention is described below in detail. As for conductive materials, those used for LSI are illustrated: for examples, Al, Al-Si(1-5%) alloy, Al-Si(1-5%)-Cu(1-5% alloy, Cu, W, Mo, WSi$_2$, MoSi$_2$, TiSi$_2$ and polysilicon. The interconnectors with stacked layer structure of different materials mentioned above, for example, those stacked alternatively with Al layer and a high melting-point metal layer such as Ti, are also used. In addition, superconductive materials can also used.

As a substrate, a Si wafer, a Si wafer having silicon oxide film of 0.1–1.0 μm in thickness on the surface, a glass substrate, a ceramics substrate made of e.g. alumina, or a copper substrate having an insulating film such as $SiO_2$ on the surface is used. A copper substrate has high cooling efficiency due to high thermal conductivity, which enables the test with higher current density.

A conductive material thin film of 0.7–1.0 μm is formed on the substrate by, for example, evaporation, sputtering, CVD or MOCVD and then etched to have a plural of patterns of e.g. 100 μm to 1 mm in length and 0.3 to 1.0 μm in width.

Any substrate supporting means is used as long as it can support the substrate and can be mounted on the cooling means. For example, a copper plate, aluminum plate or ceramic plate having a larger diameter than the substrate and a thickness of 2–5 mm is used. A copper plate is particularly preferable because the thermal conductivity of copper is high as compared with other materials.

A substrate is, for example, adhered to the substrate supporting means with a low melting-point metal such as indium. The substrate supporting means may hold a plurality of substrates and a printed board used to connect interconnector patterns with a power supply or measuring instruments.

A first current supply means to apply a first electric current to interconnectors is composed of a connecting means such as wire bonding for connecting the bonding pads of interconnectors with the corresponding pads of a printed board, a DC or AC power supply, and a connecting means such as a connector for connecting pins of a printed board with the power supply.

A means for measuring the resistance is composed of a connecting means such as a wire bonding for connecting the bonding pad of the interconnector patterns with the corresponding bonding pads of a printed board, a voltmeter, and a connecting means such as a connector for connecting pins of a printed board with the voltmeter.

A second current supply means to apply a second electric current which is larger than a first electric current has the structure similar to a first current supply means. Therefore, a first and a second current supply means can share one means for applying current to interconnectors.

For the second current supply means, both DC and AC current supplies can be used. In the case of AC current supply, various types of AC such as sine wave, pulse or alternating current superimposed on DC current can be used.

In this invention, a substrate cooling means shown in FIG. 1, for example, can be used. In the figure, a substrate 1, a printed board 2 and a substrate supporting means are also shown. The substrate cooling means is composed of a vessel 4, an inlet 5 and an outlet 6 of coolant, a coolant flow rate controller 9, a flow meter 10, and a coolant temperature controller 11 for controlling the temperature of coolant.

The inlet 5 is connected to a coolant introducing pipe 7 inside the vessel 4. A nozzle of the pipe 7 is located just under the substrate support means 3 to remove extra heat generating at the interconnectors. In the vessel, a partition plate 8 is installed surrounding the pipe 7 to prevent air retention. The outlet 6 is mounted at the lower position than the upper end of the partition and connected to the inlet of the temperature controller 11 through an heat insulating pipe 12. The inlet of coolant 5 is connected to the outlet of the temperature controller 11 through the flow meter 10, the flow rate controller 9 and an heat insulating pipe 12.

As a temperature detector, any detectors can be used as long as they can detect the temperature of interconnectors. For example, the temperature of the interconnector can be measured using the second current supply means and the means for measuring the resistance of interconnector. Namely, the temperature can be obtained by comparing the resistance which is measured as a second current is being applied with the temperature coefficient of specific resistance of the interconnector which has been obtained beforehand. In addition, contact type thermometers such as a thermocouple and non-contact type thermometers such as a pyroelectric element and a thermopile can also used.

A cooling capacity controller is composed of a coolant flow rate controller and a coolant temperature controller. The flow rate controller and the temperature controller are installed in order to maintain the interconnector at a prescribed temperature by adjusting flow rate and temperature of coolant depending upon the output signals of the temperature detector. As the flow rate controller, any valves can be used. Electromagnetic valves are preferably used because the flow rate can be controlled by output signals of the temperature detector. As a coolant temperature controller, a thermostat is, for example, preferably used, which has a heater and a cooler to control the coolant temperature by the use of output signals of the temperature detector.

Figure 2:
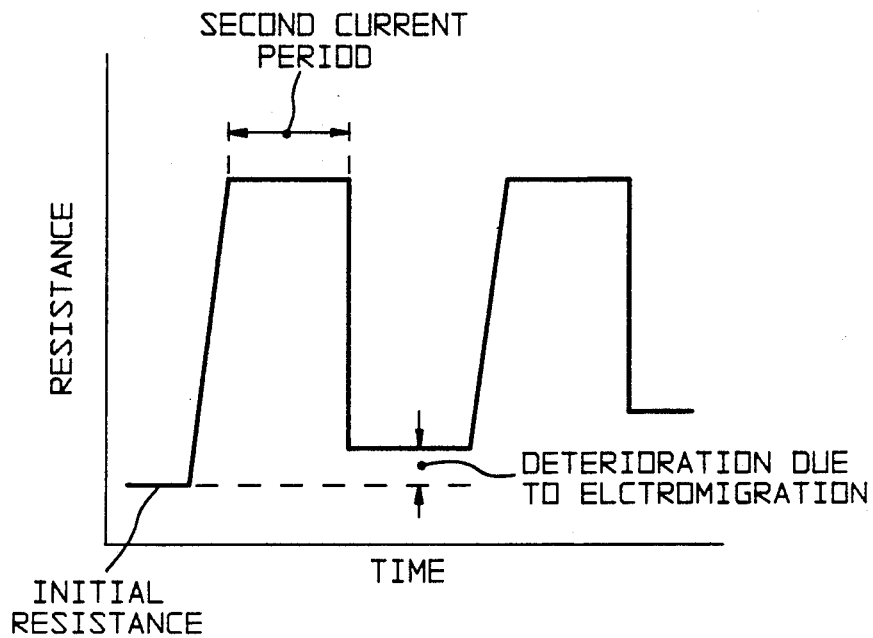
FIG. 2 is a graph showing the change of the resistance when a first and a second current are applied.

The method to obtain the life of the interconnectors against electromigration is explained by referring to FIG. 2. FIG. 2 represents resistance change of the interconnector when a first and a second current are repeatedly applied.

A current of $10^4$–$10^6$ A/cm$^2$ is applied to the interconnector as a first current and an initial value of the resistance is obtained from the voltage difference between both ends of the pattern. Then, the current is gradually increased to a second current so that the temperature of the interconnector rises to a prescribed value. The value of the stress current (second current) is determined according to material and temperature. To carry out the test at different temperature, it is also possible to change the coolant temperature.

In FIG. 2, a sharp rise of resistance is observed when a second current is applied. This is attributed to the rise of the temperature of the interconnector.

After a second current of $10^6$–$10^9$ A/cm$^2$ is applied for a prescribed period, the current is dropped instantly to a first current. The temperature of the interconnector decreases to that of coolant and therefore the resistance also decreases. The resistance becomes larger than the initial value as a result of electromigration.

As these operations are repeated, the resistance increases gradually. The life of interconnector is, for example, defined as a elapsed time by which the resistance increases, for example, 5 or 10% from initial value.

In the present invention, both DC and AC current can be used as a first current. In the case of AC, the electromigration effect taking place during the measurement of the resistance is suppressed.

The life of the interconnector determined by electromigration is given by the empirical equation (1).

$$\tau = A/J^n \times \exp(E/kT) \qquad (1)$$

(usually $n \div 2$)

τ; life
k; Boltzmann constant
T; temperature (°K)
J; current density
E; activation energy
A; constant.

Two unknown constants A and E in equation (1) are determined by carrying out above mentioned tests at two different temperatures. Then, the value of the product of the life and the current density, $J^{2*}\tau$, can be obtained at any temperature. For example, the life at a certain current density or the maximum permissible current density for required life can be estimated.

As mentioned above, in the present testing method and apparatus, extra heat generating during the application of the second current can effectively be removed by a substrate cooling means, resulting in that the interconnector can be maintained at any temperature and the resistance change only due to electromigration can be also obtained.

Furthermore, higher current density can be applied and therefore a test of the resistance to electromigration can be carried out at higher temperature. As a result, it becomes possible to shorten the test period to 1-2 hours.

An Al film of 1 μm thick is formed by sputtering or evaporation on a Si wafer with 0.5 μm thick thermal oxide film. Then, the Al film was etched to form 100 Van der Pauw patterns per substrate which had the dimension of 1 μm × 1 mm. A silicon oxide film of 1 μm thick was formed on the wafer by a CVD method. Then the portions of the film on the pads were removed by etching and the wafer was diced to substrates.

The substrate thus prepared and a ceramics printed board having bonding pads and pins were adhered to a copper plate of 50 mm in diameter and 2 mm in thickness with indium. Then, the pads of the interconnectors on the substrate were connected to the corresponding pads of the printed board by wire bonding. The copper plate is fixed as shown in FIG. 1 with screws (not shown) on the cooling vessel through an o-ring (not shown). The coolant inlet and outlet of the vessel were connected to a thermostat so that the coolant was always maintained at a prescribed temperature.

Figure 3:
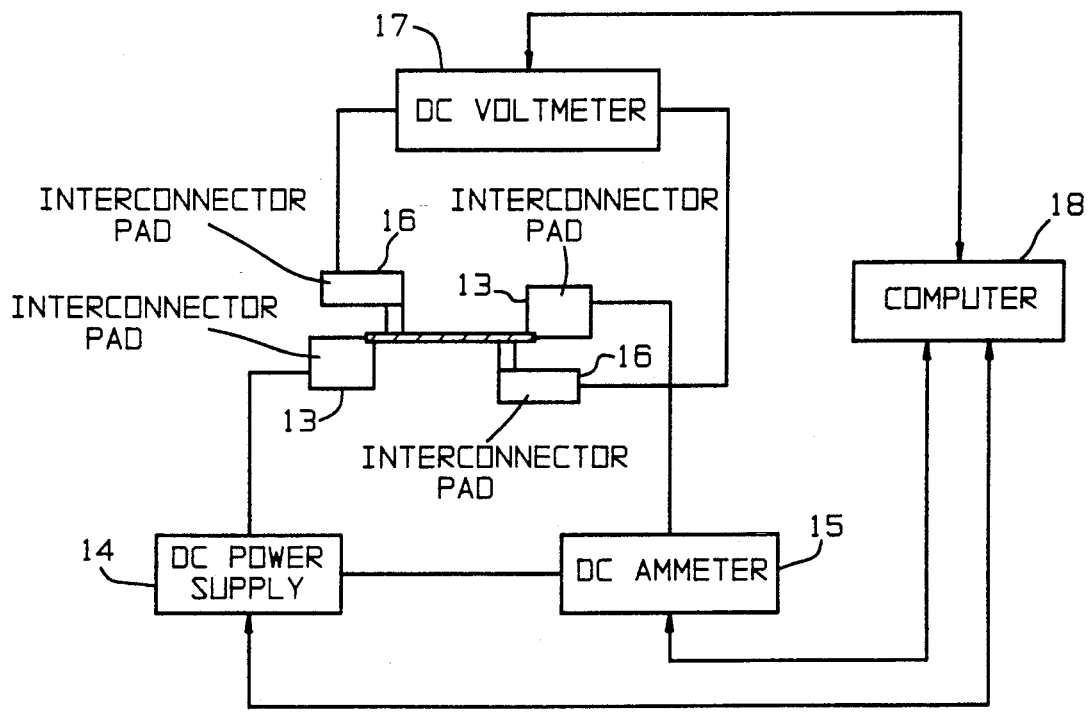
FIG. 3 is a block diagram showing the structure of the testing system.

As is shown in FIG. 3, a first pair 13 of pads of interconnection was connected to a DC power supply 14 and a DC ammeter 15 in series. A second pair 16 was connected to a DC voltmeter. In this embodiment, input and output signals of the DC voltmeter, DC power supply and DC ammeter were connected with a computer 18 so that the a first and a second currents, their on-off timing, the calculation of the resistance and the temperature of the interconnector, and the temperature of coolant could be directly controlled by the computer.

Then, the life of the interconnector was obtained in the following way. First, the resistance of each interconnector was measured as a first current was applied. Next, the current was increased to a second current corresponding to a prescribed temperature and remained for one minute. Then, the current was decreased to a first current and the resistance was measured again. These operations with a period of 3 minutes were repeated until the resistance increased 5% from initial value.

The temperature of interconnectors formed by evaporation were set to be at 80°, 110°, 140° C. by adjusting the temperature of coolant and the value of the second current. The values of a first and a second current were $1 \times 10^4$ A/cm² and $1.04-1.12 \times 10^7$ A/cm², respectively.

As to sputtered films, the temperature were set to be at 220°, 235°, 250° C. The values of a first and a second currents were $1 \times 10^4$ A/cm² and $2.16-2.74 \times 10^7$ A/cm², respectively.

Average elapsed times by which the resistance increased 5% are shown in Table 1.

TABLE I

| Temperature of Interconnector (°C.) | Lifetime of Evaporated Film (min.) | Temperature of Interconnector (°C.) | Lifetime of Sputtered Film (min.) |
| --- | --- | --- | --- |
| 80 | 200 | 220 | 150 |
| 110 | 54 | 235 | 158 |
| 140 | 19 | 250 | 66 |

Figure 4A:
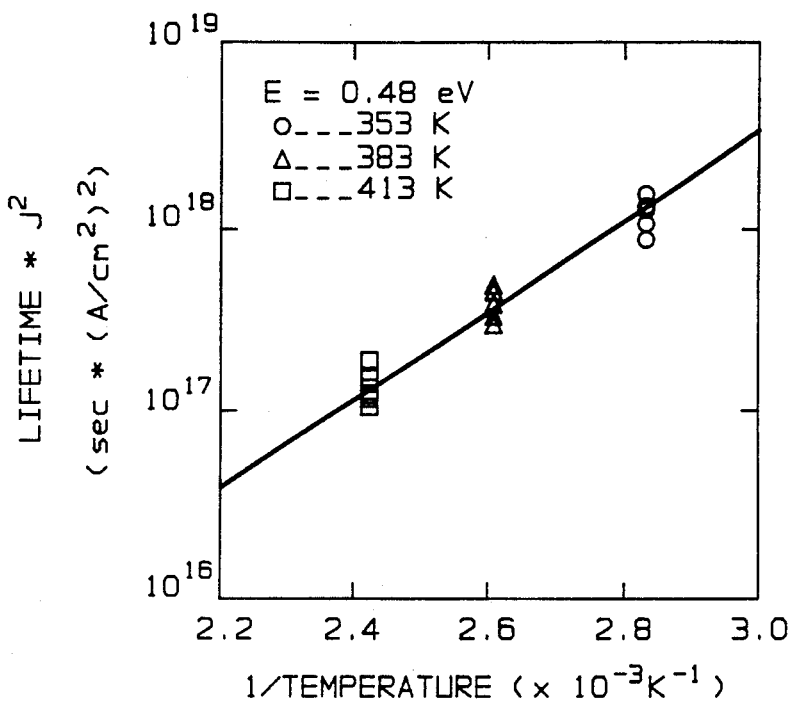
FIGS. 4(a) and 4(b) are graphs respectively showing the value of J$^2$*τ of Al evaporated films and sputtered films at various temperature.
Figure 4B:
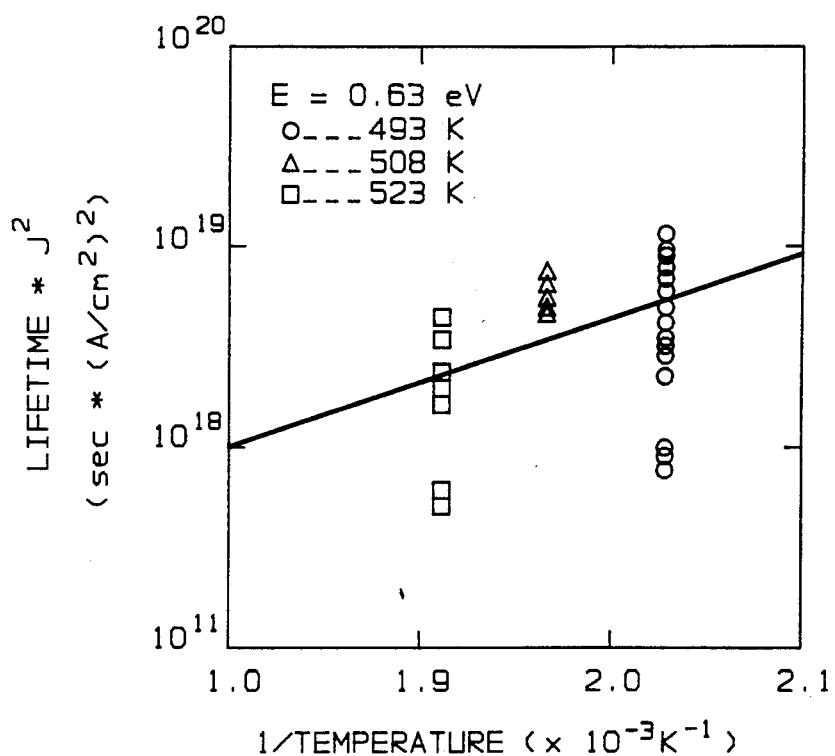

The values of $\text{Log}(J^{2*}\tau)$ were calculated and plotted in FIG. 4 as a function of 1/T. The line in the figure was obtained by the least squares method from the average values of the data at each temperature. From the line of FIG. 4, the value of $J^{2*}\tau$, the product of the square of current and the life, can be obtained at any temperature. Therefore, it can be calculated that the maximum current density for the life of interconnectors of ten years at room temperature (300° K.) is $2.6 \times 10^5$ A/cm² for the evaporated film (FIG. 4(a)) and $1.5 \times 10^7$ A/cm² for the sputtered film (FIG. 4(b)).

These results are in good agreement with the results obtained by a conventional method which are $1.5-3.5 \times 10^5$ A/cm² and $0.7-2.5 \times 10^7$ A/cm² for evaporated films and sputtered films, respectively.

The times spent in the test by the present method and the conventional method for the sputtered film were 20-200 minutes and one month, respectively, showing that the method of the present invention has very high efficiency.

The present invention makes it possible to provide an apparatus for evaluating the electromigration resistance of interconnector materials in short time and greatly contribute to the material development.

I claim:

1. A method for measuring the resistance of a conductive material to electromigration, comprising the steps of:

providing an interconnector pattern made of a conductive material and being at a first temperature;

applying a first electric current to the interconnector pattern, wherein the applied current does not substantially heat the interconnector pattern to measure a first value of resistance of the interconnector pattern;

applying a second current to the interconnector pattern for a given period of time, wherein the second current is greater than the first current as maintaining the interconnector pattern at a substantially constant second temperature during the given period of time by cooling the interconnector pattern sufficiently to offset the effects of joule heating;

cooling the interconnector pattern to said first temperature after the given period of time;

applying the first electric current to the interconnector pattern to measure a second value of resistance of the interconnector pattern; and subtracting the first value from the second value to determine a difference of resistance, said difference being attributable to electromigration.

2. The method of claim 1, wherein the steps of applying a second current, cooling the interconnector pattern, applying the first electric current, and subtracting the first value from the second value are repeated until said second value of resistance is greater than said first value by a given amount.

3. The method of claim 2, wherein said given amount is 5 percent.

4. An apparatus for measuring the resistance of a conductive material to electromigration, comprising:
a substrate support for supporting a substrate;
an interconnector pattern comprising a conductive material formed on said substrate;
said substrate support being mounted on a cooling means for cooling said substrate support and said substrate;
first current supply means in electrical communication with said interconnector pattern for applying a first current to said interconnector pattern;
second current supply means in electrical communication with said interconnector pattern for applying a second electric current larger than said first electric current to said interconnector pattern, said second current being applied after said first current supply means is first applied;
resistance measuring means in electrical communication with said interconnector pattern for measuring the resistance of said interconnector pattern while said first current is being applied to said interconnector pattern; and
a controller for controlling at least said first current supply means, said second current supply means, and said resistance measuring means so that the measurement of the resistance of said interconnector pattern and the application of said second electric current to cause electromigration are repeatedly carried out.

5. The apparatus of claim 4, including a temperature detector arranged to detect the temperature of said interconnector pattern while said second electric current is being applied thereto, said temperature detector configured to output a temperature signal to said cooling means by which the temperature and the flow rate of cooling liquid in said cooling means are controlled to maintain said interconnector pattern at a given temperature.

6. A testing apparatus according to claim 5, wherein said temperature detector comprises a means for measuring the resistance of said interconnector pattern while said second electric current is being applied and a means for converting resistance to temperature.

7. A testing apparatus according to claim 4, wherein said cooling means has a vessel with an outlet of coolant, a partition plate, at least a portion of which is lower than the outer wall of said vessel, and a nozzle which the coolant is ejected from and which is located just beneath said substrate support.

8. A testing apparatus according to claim 4, wherein said second current is $10^6$–$10^9$ A/cm$^2$.

9. A testing apparatus according to claim 5 wherein said cooling means has a vessel with an outlet of coolant, a partition plate, at least a portion of which is lower than the outer wall of said vessel, and a nozzle which the coolant is ejected from and which is located just under said substrate support.

10. A testing apparatus according to claim 6, wherein said cooling means has a vessel with an outlet of coolant, a partition plate, at least a portion of which is lower than the outer wall of said vessel, and a nozzle which the coolant is ejected from and which is located just under said substrate supporting means.

11. A testing apparatus according to claim 5, wherein said second current is $10^6$–$10^9$ A/cm$^2$.

12. A testing apparatus according to claim 6, wherein said second current is $10^6$–$10^9$ A/cm$^2$.

13. A testing apparatus according to claim 7, wherein said second current is $10^6$–$10^9$ A/cm$^2$.

* * * * *